United States Patent
Zhenzhen et al.

(10) Patent No.: US 6,193,995 B1
(45) Date of Patent: Feb. 27, 2001

(54) HERBAL MIXTURE FOR TREATING NASAL CONGESTION

(76) Inventors: Zhang Zhenzhen; Deguang He, both of 37 Crescent St., Newton, MA (US) 02465

(*) Notice: Subject to any disclaimer, the term of this patent is extended or adjusted under 35 U.S.C. 154(b) by 0 days.

(21) Appl. No.: 09/275,127

(22) Filed: Mar. 24, 1999

(51) Int. Cl.⁷ .................. A61F 13/02; A61F 2/02; A61K 9/70; A61K 39/385
(52) U.S. Cl. .................. 424/449; 424/423; 424/443; 424/195.1
(58) Field of Search .................. 424/195.1, 423, 424/443, 449

(56) References Cited

U.S. PATENT DOCUMENTS

| | | |
|---|---|---|
| 4,886,655 | 12/1989 | Kovacs . |
| 5,248,503 | 9/1993 | King . |
| 5,648,089 | 7/1997 | Shawkat . |
| 5,766,614 | 6/1998 | Yong . |

*Primary Examiner*—Carlos A. Azpuru

(57) ABSTRACT

A herbal mixture (10) to treat a user (16) for nasal congestion, the herbal mixture (10) comprises a plurality of herbs (14) throughly mixed together and combined with an adhesive. The plurality of herbs (14) comprise Fructus *Piperis nigri* herb (14A ), Rhizoma *Zingiberis officinalis* herb (14B), and Ramulus Cinnamomi Cassiae herb (14C). The Fructus *Piperis nigri* herb (14A) is in a range from 0.1% to 99.8%. The Fructus *Piperis nigri* herb (14A) is preferably 33.3%. The Rhizoma *Zingiberis officinalis* herb (14B) is in a range from 0.1% to 99.8%. The Rhizoma *Zingiberis officinalis* herb (14B) is preferably 33.3%. The Ramulus Cinnamomi Cassiae herb (14C) is in a range from 0.1% to 99.8%. The Ramulus Cinnamomi Cassiae herb (14C) is preferably 33.3%.

10 Claims, 3 Drawing Sheets

HERBAL MIXTURE FOR TREATING NASAL CONGESTION

BACKGROUND OF THE INVENTION

1. Field of the Invention

The present invention relates to herbal remedies. More particularly, the present invention relates to application of herbs in the form of a bandage.

2. Description of the Prior Art

Numerous innovations for herbal mixture have been provided in the prior art that are described as follows. Even though these innovations may be suitable for the specific individual purposes to which they address, they differ from the present invention as hereinafter contrasted.

In U.S. Pat. No. 5,766,614, titled Burn Treatment Compositions Containing Herbal Mix, invented by Liu Yong, a new Burn Treatment Composition which provides healing to the skin of people who have received burns or are afflicted with other skin complications that require healing. The inventive device includes effective amounts of Chinese rhubarb, calcium hydroxide, *Sanguisorba officinalis* rhizome, common camphor, *Coptis chinensis* rhizome, *Phellodendron amurense* bark and *Oldenlandia diffusa* roxd.

The patented invention differs from the present invention because the patented invention includes effective amounts of Chinese rhubarb, calcium hydroxide, *Sanguisorba officinalis* rhizome, common camphor, *Coptis chinensis* rhizome, *Phellodendron amurense* bark and *Oldenlandia diffusa* roxd. The present invention is a kind of herbal bandage made of mixture of White Pepper, Dried Ginger Rhizome and Cinnamon Twig powder combined with adhesive.

In U.S. Pat. No. 5,648,089, titled Extract Solution and Herbal Mixture for Treatment of Hepatiti, invented by Tarek Shawkat, a newly formulated herbal mixture and herbal nasal drops are provided for ethical use and treatment of vital hepatitis diseases. The herbal formulation is in two parts, which may be used separately or together, including (1) an oral herbal formulation including coarse granules of 9 herbs, ground and added together in specific ratios, and (2) nasal drops prepared from the extract of a single herb, namely *Ecballium Elaterium* A. Rich.

The patented invention differs from the present invention because the patented invention is a mixture of an oral herbal formulation including coarse granules of 9 herbs, ground and added together in specific ratios, and (2) nasal drops prepared from the extract of a single herb, namely *Ecballium elaterium* A. Rich. The present invention is a kind of herbal bandage made of mixture of White Pepper, Dried Ginger Rhizome and Cinnamon Twig powder with adhesive.

In U.S. Pat. No. 5,248,503, titled Herbal Dietary Supplement, invented by Rosalba Emanuel-King, a dietary supplements is described containing in solution at least two herbal ingredients selected from a group consisting of: mullen leaf, witch hazel, baptisia (wild indigo), marshmallow root (*Althea officianales*), *Potentilla tormentilla,* myrrh, agrimony, blood root (sanguinaria), bistort, echinacea, parsley, eucalyptus, wintergreen, rosemary, ginger, sandalwood, sweet almond, sassafrass, linseed and castor. When ingested transcutaneously the product is holistically effective for reduction of plaque and for treating symptons of gingivitis, gum disorders, cold sores, oral boils, herpes simplex, pimples and acne vulgaris. The holistic product is carried in a treatment medium which may be a liquid solution, drops, gum drops, lozenges, chewing gum, breath dots, toothpaste, a skin patch, an oral rinse, a cream, a poultice, a suppository, a vapor, an inhalter and/or a douche.

The patented invention differs from the present invention because the patented invention is contains in solution at least two herbal ingredients selected from a group consisting of: mullen leaf, witch hazel, baptisia (wild indigo), marshmallow root (*Althea officianales*), *Potentilla tormentilla,* myrrh, agrimony, blood root (sanguinaria), bistort, echinacea, parsley, eucalyptus, wintergreen, rosemary, ginger, sandalwood, sweet almond, sassafrass, linseed and castor. The patented invention is ingested. The present invention is a kind of herbal bandage made of mixture of White Pepper, Dried Ginger Rhizome and Cinnamon Twig powder with adhesive. The present invention includes a method of use having the following steps:

i) locate Yintang (position between the eyebrows)
ii) locate a point on the top left outside of nostril
iii) locate a point on the top right outside of nostril
iv) apply an oval bandage to each located point In U.S. Pat. No. 4,886,665, titled Compositions of Oats and Nettle Extracts to Be Used as a Food Additive or Pharmaceutic Preparation in Human Health Care, invented by Joseph Kovacs, a food supplement composition is described containing an oat extract and an extract of nettle (Urtica). The combined extracts can be in the form of powder which is added to a beverage or any fruit juice to provide a nutritional drink. The composition can also be used for the treatment of a dysfunction of a warm blooded mammal. The products can be taken in various forms such as dried powdered mix with a liquid, as a pill, tablet, capsule, or for nasal delivery.

The patented invention differs from the present invention because the patented invention is an oat extract and an extract of nettle (Urtica). The combined extracts are added, in the form of powder, to a beverage or any fruit juice to provide a nutritional drink. The patented invention is formed into dried powdered mix with a liquid, as a pill, tablet, capsule, or for nasal delivery. The patented invention lacks features similar to the present invention.

Numerous innovations for a herbal mixture have been provided in the prior art that are adapted to be used. Even though these innovations may be suitable for the specific individual purposes to which they address, they would not be suitable for the purposes of the present invention as heretofore described.

SUMMARY OF THE INVENTION

The present invention is a kind of herbal bandage made of a mixture of White Pepper, Dried Ginger Rhizome and Cinnamon Twig powder with adhesive. The present invention includes a method of use having the following steps:

i) locate Yintang
ii) locate a point on the top left outside of nostril
iii) locate a point on the top right outside of nostril
iv) apply an oval bandage to each located point The types of problems encountered in the prior art are application of herbal remedies to a local area of the skin without mixing.

In the prior art, unsuccessful attempts to solve this problem were attempted namely solutions, powders and lotions were applied to the skin. However, the problem was solved by the present invention because the herbs are applied to a bandage, after application to the skin the herbs are absorbed into the skin from the bandage.

Innovations within the prior art are rapidly being exploited as herbal remedies become increasingly popular.

The present invention went contrary to the teaching of the art which applied messy lotion, liquids and plasters to the skin.

The present invention solved a long felt need easy application of herbs to the skin.

Accordingly, it is an object of the present invention to provide a bandage having a herbal remedy therein.

More particularly, it is an object of the present invention to provide an application of the herbal mixture to the skin.

In keeping with these objects, and with others which will become apparent hereinafter, one feature of the present invention resides, briefly stated, in a bandage.

When the bandage is designed in accordance with the present invention, herbs are positioned adjacent the skin so that the herbs are absorbed into the skin.

In accordance with another feature of the present invention a bandage back adhesive functions to removably attach the bandage to the skin.

Another feature of the present invention is that a bandage back absorber functions to contain a plurality of herbs.

Yet another feature of the present invention is that a bandage top is provided to protect the herbs from moisture and dirt.

Still another feature of the present invention is that herbs are contained in an absorber.

Yet still another feature of the present invention is that the herbs are Fructus *Piperis nigri* herb, Rhizoma *Zingiberis officinalis* herb, and Ramulus Cinnamomi Cassiae herb.

Still yet another feature of the present invention is that the bandage is applied to a user's acupuncture points midway between the user's eyebrows.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings.

List of Reference Numerals Utilized in the Drawings

10—herbal mixture (10)
12—bandage (12)
12B—bandage back (12B)
12BA—bandage back adhesive (12BA)
12BB—bandage back absorber (12BB)
12T—bandage top (12T)
14—herbs (14)
14A—Fructus *Piperis nigri* herb (14A)
14B—Rhizoma *Zingiberis officinalis* herb (14B)
14C—Ramulus Cinnamomi Cassiae herb (14C)
16—user (16)
16F—user's face (16F)
16L—user's left eyebrow (16L)
16R—user's right eyebrow (16R)
16M—user's middle (16M)
16N—user's nose (16N)
16NL—user's nose left nostril (16NL)
16NR—user's nose right nostril (16R)

DESCRIPTION OF THE PREFERRED EMBODIMENT

Figure 1:
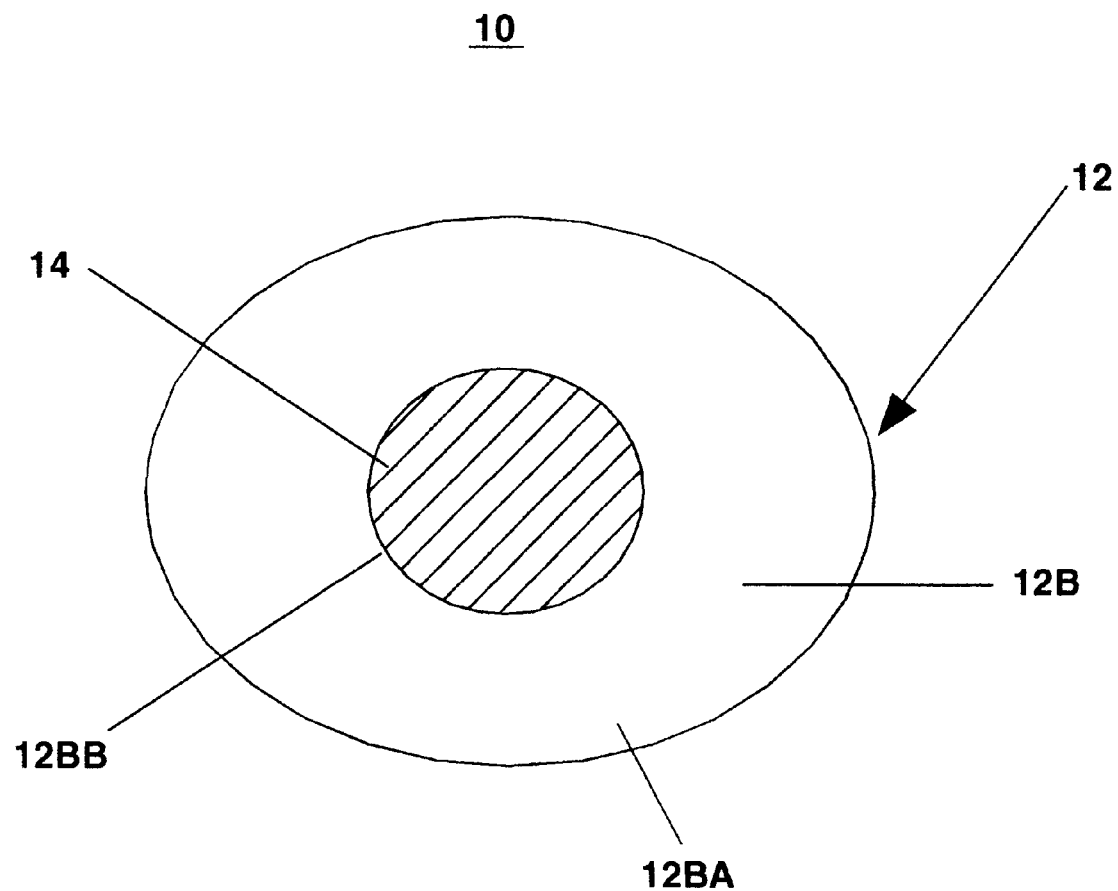
FIG. 1 is view of a bandage back.

Firstly, referring to FIG. 1 which is view of a bandage back (12B) having a herbal mixture (10) to treat a user (16) for nasal congestion. The herbal mixture (10) comprises a plurality of herbs (14) throughly mixed together in combination with a bandage back adhesive (12BA). The plurality of herbs (14) comprise Fructus *Piperis Nigri* herb (14A), Rhizoma *Zingiberis officinalis* herb (14B), and Ramulus Cinnamomi Cassiae herb (14C). The Fructus *Piperis nigri* herb (14A) is in a range from 0.1% to 99.8%. The Fructus *Piperis nigri* herb (14A) is preferably 33.3%. The Rhizoma *Zingiberis officinalis* herb (14B) is in a range from 0.1% to 99.8%. The Rhizoma *Zingiberis officinalis* herb (14B) is preferably 33.3%. The Ramulus Cinnamomi Cassiae herb (14C) is in a range from 0.1% to 99.8%. The Ramulus Cinnamomi Cassiae herb (14C) is preferably 33.3%.

The herbal mixture (10) further comprises at least one bandage (12). The at least one bandage (12) comprises a bandage back (12B) having bandage back adhesive (12BA) and a bandage top (12T). The plurality of herbs (14) throughly mixed together in combination with a bandage back adhesive (12BA) is placed uniformly over the bandage back (12B). The bandage (12) is placed on a user's face (16F) over at least one of three acupuncture points selected from a group consisting of Yintang located at a user's middle (16M) between a user's left eyebrow (16L) and a user's right eyebrow (16R), Large Intestine (20) located on top of a user's nose left nostril (16NL) on a user's nose (16N), and Large Intestine (20) located on top of a user's nose right nostril (16R). The bandage (12) comprises an configuration selected from a group consisting of; round, oval, square, rectangular and trapezoidal.

The at least one bandage (12) may be three bandage (12) each positioned on one of the three acupuncture points selected from a group consisting of Yintang located at a user's middle (16M) between a user's left eyebrow (16L) and a user's right eyebrow (16R), Large Intestine (20) located on top of a user's nose left nostril (16NL) on a user's nose (16N), and Large Intestine (20) located on top of a user's nose right nostril (16R).

Figure 1A:
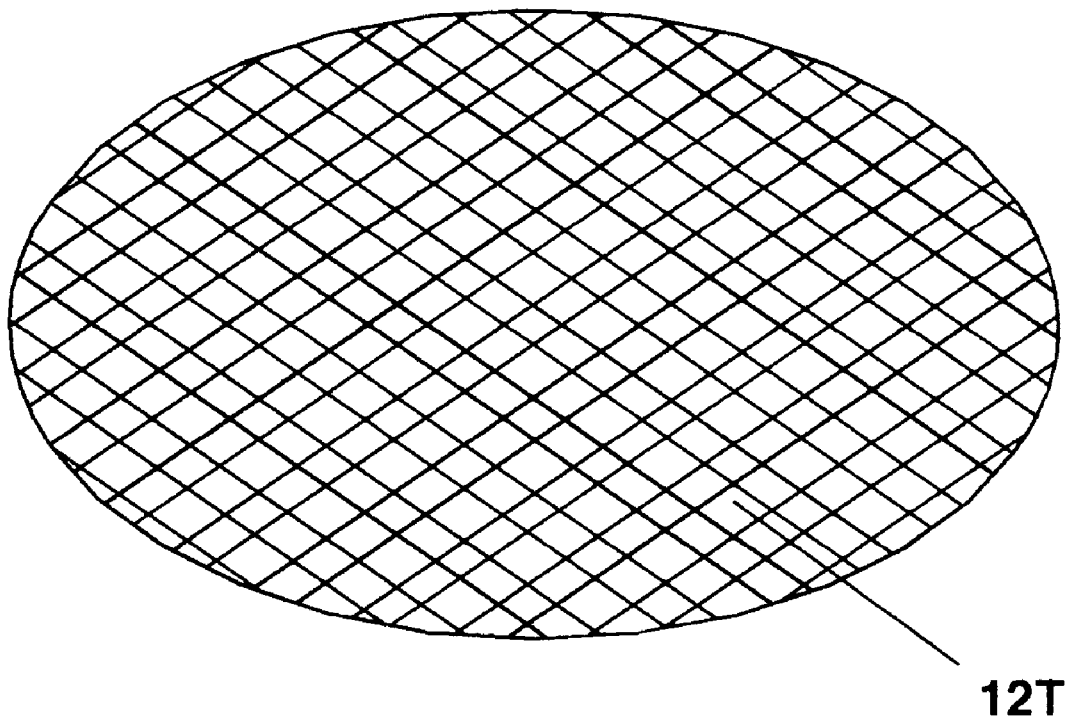
FIG. 1A is view of a bandage top.

Secondly, referring to FIG. 1A which is view of a bandage top (12T). The bandage top (12T) functions to protect the bandage back (12B) having bandage back adhesive (12BA) from dirt and contaminants.

Figure 2:
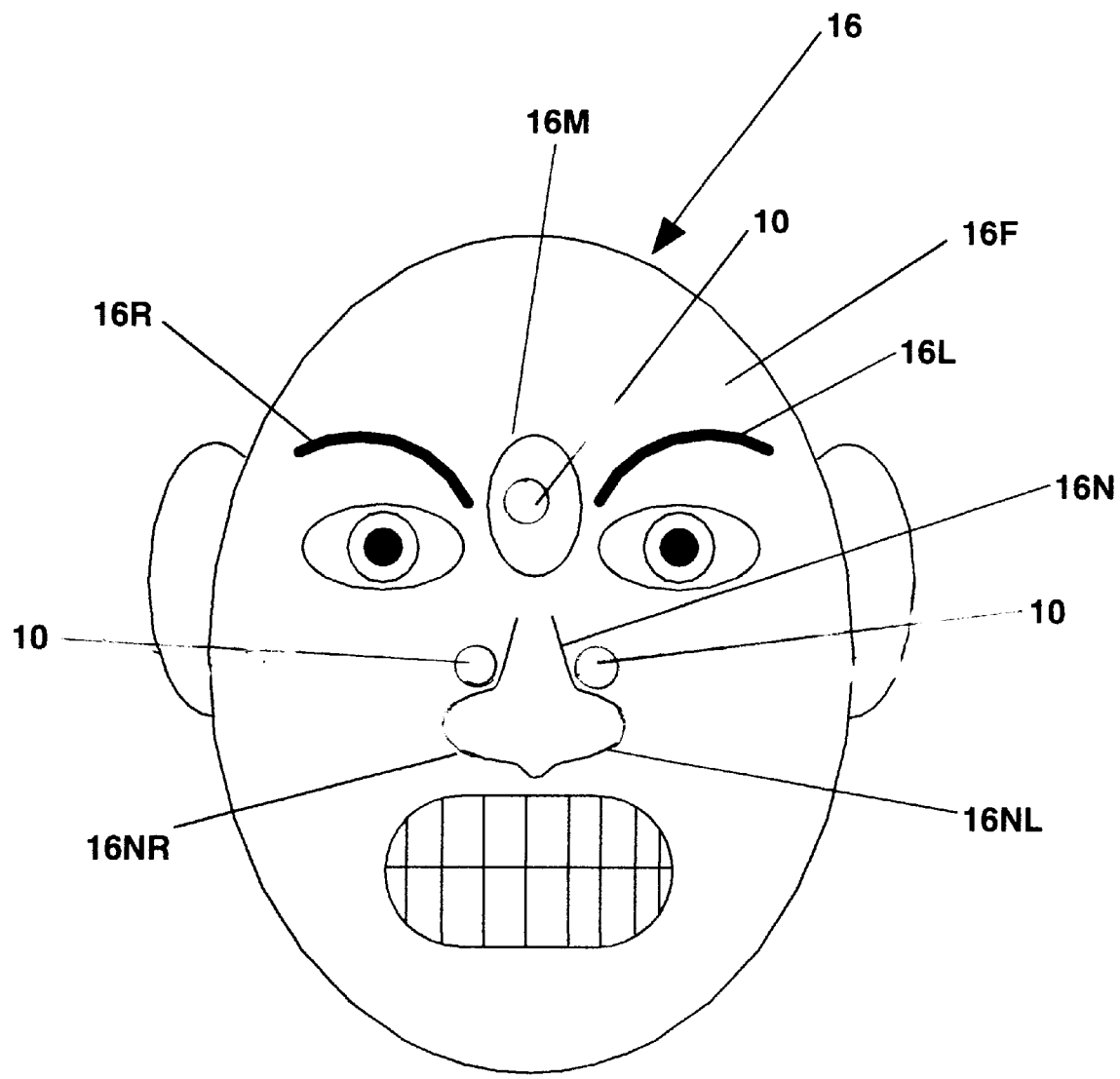
FIG. 2 is a view of a user's face exhibiting acupuncture points.

Lastly, referring to FIG. 2 which is a view of a user's face (16F) exhibiting acupuncture points. The bandage (12) is placed on a user's face (16F) over at least one of three acupuncture points selected from a group consisting of Yintang located at a user's middle (16M) between a user's left eyebrow (16L) and a user's right eyebrow (16R), Large Intestine (20) located on top of a user's nose left nostril (16NL) on a user's nose (16N), and Large Intestine (20) located on top of a user's nose right nostril (16R). The at least one bandage (12) may be three bandages (12) each positioned on one of the three acupuncture points selected from a group consisting of Yintang located at a user's middle (16M) between a user's left eyebrow (16L) and a user's right eyebrow (16R), Large Intestine (20) located on top of a user's nose left nostril (16NL) on a user's nose (16N), and Large Intestine (20) located on top of a user's nose right nostril (16R).

It will be understood that each of the elements described above, or two or more together, may also find a useful application in other types of constructions differing from the type described above.

While the invention has been illustrated and described as embodied in a herbal mixture, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A herbal mixture (10) to treat a user (16) for nasal congestion, the herbal mixture (10) comprising:
    A) a plurality of herbs (14) consisting of Fructus *Piperis nigri* herb (14A), Rhizoma *Zingiberis officinalis* herb (14B), and Ramulus Cinnamomi Cassiae herb (14C) throughly mixed together.

2. The herbal mixture (10) as described in claim 1, wherein the Fructus *Piperis nigri* herb (14A) is in a range from 0.1% to 99.8%.

3. The herbal mixture (10) as described in claim 2, wherein the Fructus *Piperis nigri* herb (14A) is preferably 33.3%.

4. The herbal mixture (10) as described in claim 1, wherein the Rhizoma *Zingiberis officinalis* herb (14B) is in a range from 0.1% to 99.8%.

5. The herbal mixture (10) as described in claim 4, wherein the Rhizoma *Zingiberis officinalis* herb (14B) is preferably 33.3%.

6. The herbal mixture (10) as described in claim 1, wherein the Ramulus Cinnamomi Cassiae herb (14C) is in a range from 0.1% to 99.8%.

7. The herbal mixture (10) as described in claim 6, wherein the Ramulus Cinnamomi Cassiae herb (14C) is preferably 33.3%.

8. The herbal mixture (10) as described in claim 1 further comprises at least one bandage (12) which comprises a bandage back (12B) having bandage back adhesive (12BA) and a bandage top (12T), the herbal mixture (10) is made of a mixture of White Pepper, Dried Ginger Rhizome and Cinnamon Twig powder combined with adhesive, the herbal mixture (10) combined with adhesive is placed uniformly over the bandage back (12B), the bandage (12) is placed on a user's face (16F) over at least one of three acupuncture points selected from a group consisting of Yintang located at a user's middle (16M) between a user's left eyebrow (16L) and a user's right eyebrow (16R), Large Intestine (20) located on top of a user's nose left nostril (16NL) on a user's nose (16N), and Large Intestine (20) located on top of a user's nose right nostril (16R).

9. The herbal mixture (10) as described in claim 8, wherein the bandage (12) comprises an oval configuration.

10. The herbal mixture (10) as described in claim 8, wherein the at least one bandage (12) are three bandage (12) each positioned on one of the three acupuncture points selected from a group consisting of Yintang located at a user's middle (16M) between a user's left eyebrow (16L) and a user's right eyebrow (16R), Large Intestine (20) located on top of a user's nose left nostril (16NL) on a user's nose (16N), and Large Intestine (20) located on top of a user's nose right nostril (16R).

* * * * *